(12) United States Patent
Schulte

(10) Patent No.: US 8,920,315 B2
(45) Date of Patent: Dec. 30, 2014

(54) QUICK-ACTION TENSIONING CLIP OF A WOUND RETRACTOR

(75) Inventor: Hermann-Josef Schulte, Salzkotten (DE)

(73) Assignee: Condor GmbH Medicaltechnik, Salzkotten (DE)

( * ) Notice: Subject to any disclaimer, the term of this patent is extended or adjusted under 35 U.S.C. 154(b) by 219 days.

(21) Appl. No.: 13/141,503

(22) PCT Filed: Dec. 22, 2009

(86) PCT No.: PCT/DE2009/001800
§ 371 (c)(1),
(2), (4) Date: Oct. 17, 2011

(87) PCT Pub. No.: WO2010/072212
PCT Pub. Date: Jul. 1, 2010

(65) Prior Publication Data
US 2012/0035424 A1 Feb. 9, 2012

(30) Foreign Application Priority Data
Dec. 22, 2008 (DE) .......................... 10 2008 064 195

(51) Int. Cl.
*A61B 1/32* (2006.01)
*A61B 17/02* (2006.01)
*A61B 17/00* (2006.01)
*A61B 19/00* (2006.01)

(52) U.S. Cl.
CPC ... *A61B 17/0206* (2013.01); *A61B 2017/00477* (2013.01); *A61B 2019/267* (2013.01)
USPC ........................................................ 600/230

(58) Field of Classification Search
USPC .................. 600/201–249; 248/229.23, 227.4, 248/227.3, 230.1, 230.4, 231.51; 403/90, 403/122–144
See application file for complete search history.

(56) References Cited

U.S. PATENT DOCUMENTS

2007/0213597 A1* 9/2007 Wooster ........................ 600/234

FOREIGN PATENT DOCUMENTS

| GB | 1 418 017 | 12/1975 |
|---|---|---|
| GB | 1 472 750 | 5/1977 |

* cited by examiner

*Primary Examiner* — Mary Hoffman
*Assistant Examiner* — Michelle C Eckman
(74) *Attorney, Agent, or Firm* — Laurence A. Greenberg; Werner H. Stemer; Ralph E. Locher

(57) ABSTRACT

A quick-action tensioning clip of a wound retractor, with at least one braceable seat for at least one holding arm and/or for a joint ball of a holding arm, is made available which can be operated safely, easily and quickly and which requires only low operating forces and at the same time safely and permanently generates high clamping forces, this being achieved by the fact that, in order to generate the tensioning force, it is equipped with a toggle catch composed of two joint levers which are connected to each other via a connecting joint and which, at their free ends, are articulated via attachment joints on component parts of the quick-action tensioning clip that can be mechanically moved away from or towards one another.

10 Claims, 3 Drawing Sheets

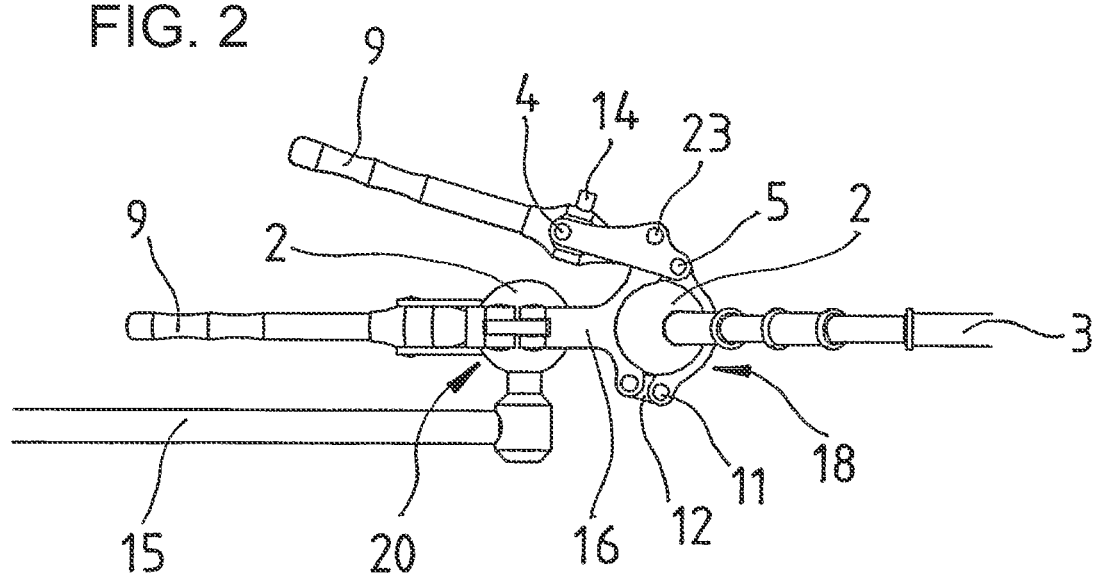
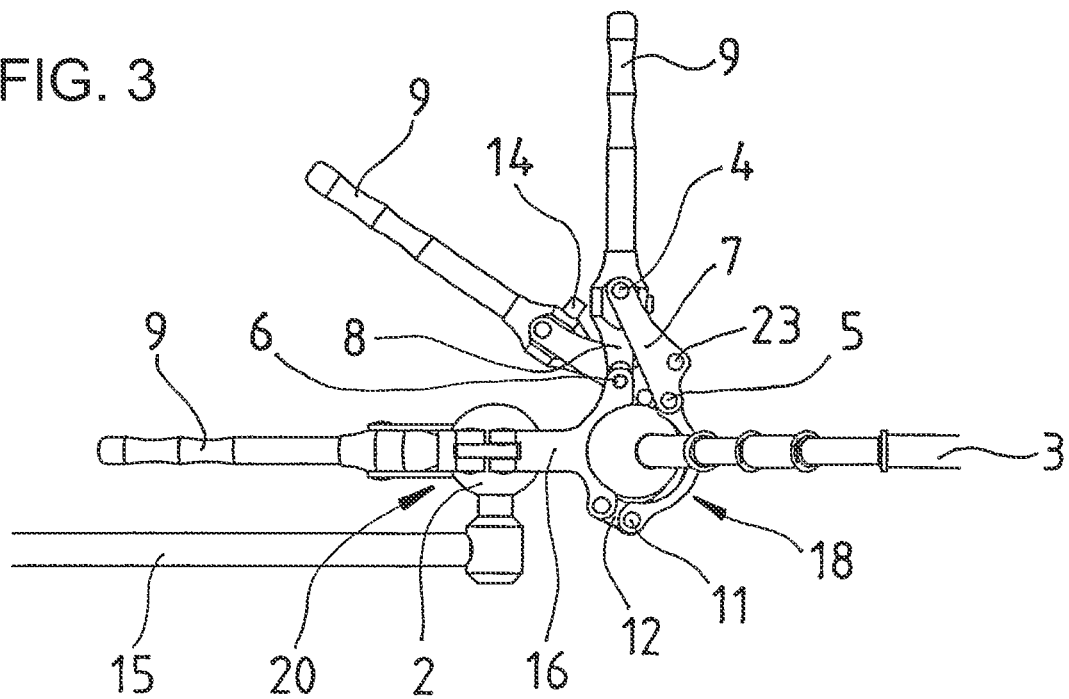

QUICK-ACTION TENSIONING CLIP OF A WOUND RETRACTOR

BACKGROUND OF THE INVENTION

Field of the Invention

The invention relates to a quick-action clamping clip of a wound retractor, comprising at least one clampable receptacle for at least one holding arm or a joint ball of a holding arm according to the preamble of the main claim.

A wound retractor which has a connecting arm to a central holder of an operating table is known from DE 19712746 C2, comprising a quick-action clamping clip which is arranged on said connecting arm and holds a shaft on which two further quick-action clamping clips are arranged, which in turn carry holding arms of the wound retractor. In this known arrangement, the clamping devices each consist of screw fasteners, which can lead to unfavorably oriented actuating levers and require a high expenditure of force for the reliable fixing of the holding arms and therefore also for the release. Other known eccentric clamping devices partly have clamping properties which are difficult to proportion and which cannot be adjusted.

BRIEF SUMMARY OF THE INVENTION

The object of the invention is to provide a quick-action clamping clip which can be operated and set reliably, simply and quickly and requires only small operating forces in the process and at the same time reliably produces high clamping forces in a lasting manner.

This object is achieved according to the invention by the features of the characterizing part of the main claim in conjunction with the features of the preamble, wherein the quick-action clamping clip, for producing the clamping force, is provided with a toggle fastener consisting of two articulated levers which are connected to one another via a connecting joint and which are linked at their free ends via attachment joints to components of the quick-action clamping clip which can be mechanically moved away from or toward one another. By means of such a toggle fastener, all the clips of wound retractors which are operated via threads or eccentrics can be redesigned in such a way that a very high clamping force can be realized with only a small expenditure of force, whether for clips for bar-shaped round holding arms or spherical joint elements of such holding arms.

A further advantage of this inventive quick-action clamping clip consists in the fact that the actuating lever only has to be moved over a small angular range in order to be brought from an adjusting position of a clamped holding or connecting arm into a very tightly clamped position, such that the actuating lever, as is the case, for example, with screw clips, requires no large free radius for actuation, said radius possibly not being available in an operating area.

Advantageous configurations of the subject matter of the invention are obtained with and in combination from the following dependent claims.

According to an especially preferred embodiment, the actuating lever which can be operated manually is embodied directly on one of the articulated levers of the toggle fastener, in particular in one piece with said articulated lever, wherein this actuating lever is oriented in alignment with the connecting joint and the attachment joint closer to said connecting joint, as a result of which the construction cost of the quick-action clamping clip is also reduced. Depending on the space conditions and installation situations which are expected to be present, such an actuating lever can also be advantageously arranged to the side of an articulated lever, a factor which substantially increases the freedom of a designer.

According to a further preferred configuration of the inventive quick-action clamping clip, the receptacle is designed like a pipe clamp which partly encloses a holding arm or a joint ball and which has attachment joints on the ends of the pipe clamp located opposite one another at only a slight distance apart, wherein the articulated levers arranged thereon both extend to a common side in an approximately tangential direction and are connected to one another there via the common connecting joint. The pivots of the joints are in alignment in a clamping position, the two pivots of the attachment joints being held pressed against one another in this aligned position.

In order to pass from this clamping position into an only slightly loosened setting position of a holding arm in the quick-action clamping clip, the pivot of the connecting joint must be deflected only slightly more in the radial direction of the actuating lever, which can be carried out with a very small expenditure of force, just as the renewed fixed clamping position can be restored with just as little expenditure of force. Surgeons with less physical strength can therefore also use the quick-action clamping clip and thus the entire wound retractor without any problems.

In particular for the exchange of holding arms or for cleaning the wound retractor, the pipe clamp, in a region opposite the attachment joints, is advantageously provided with a further joint or else with two joints connected by a coupling element, such that an opening angle of the actuating lever of about 90° already enables the pipe clamp to be opened up almost completely, such that each holding arm held therein or each joint ball can be freely removed therefrom.

In an especially preferred embodiment of the invention, three of such quick-action clamping clips are combined to form a central clip, wherein two quick-action clamping clips arranged in parallel are formed for two holding arms, which then form a wound retraction frame, and the third quick-action clamping clip is designed for fastening to a ball joint of a connecting arm to a central holder of an operating table, such that, with only a small space required overall for operating the quick-action clamping clips, as large an adjusting range of the holding arms as possible can be realized on the connecting arm.

In this case, the first articulated lever preferably consists of two spaced-apart straps which are arranged on both sides of the first attachment joint and of the connecting joint, wherein the second articulated lever is arranged between these straps and is of bar-shaped design, and a locking shaft is arranged in the common connecting joint in the second articulated lever, said locking shaft having a releasable latching device for mutually locking the movement of the two articulated levers. This latching device makes it possible for the toggle fastener, which is virtually self-locking in a clamping position when it is pivoted slightly beyond an aligned position of the common joint pivots, to be secured in a setting position of a holding arm, the setting position being pivoted only slightly in the opening direction.

Also advantageous is another band-shaped pipe clamp which likewise encloses a receptacle and has extensions which run approximately tangentially and crosswise and which carry the attachment joints at their ends, wherein two articulated levers angled relative to one another are connected to one another in between and via a common connecting joint in such a way that a compressive force is produced in the articulated levers when the three joints are in alignment, said compressive forces in turn causing tensile forces in the ends of the extensions and thus constricting the pipe clamp like a tightened band and thus producing a clamping force.

A further advantageous variant of a quick-action clamping clip can be designed in the form of spreading forceps, the actuating handles of which are provided with the attachment joints for the articulated levers, which are again connected to one another in a slightly angled manner via a common connecting joint, such that, by the three joints being brought into alignment, a clamping force can be produced on the head of the forceps, which is designed as a receptacle for a holding arm or a joint ball of a holding arm.

This basic technical principle of realizing quick-action clamping clips by means of toggle fasteners, can also be implemented for quick-action clamping clips which consist of a U-shaped basic body and the receptacles of which are arranged in the region of the free ends of the beams which are parallel to one another, wherein a clamping pin extends therebehind transversely through the beams, said clamping pin being supported on an outer side on one of the beams and having on the opposite outer side an attachment joint for an articulated lever, the second articulated lever is arranged on the beam facing this attachment joint via a second attachment joint thereon, and both articulated levers are connected to one another in a slightly angled manner by the connecting joint, such that a clamping force which compresses the receptacle is produced when the joints are brought into alignment.

All the conceivable embodiments of the inventive quick-action clamping clip enable a high clamping force to be produced with only slight travel of an actuating lever, as a result of which high operating reliability during the use of the quick-action clamping clips is ensured.

An exemplary embodiment of the invention is described in more detail with reference to drawings, in which:

BRIEF DESCRIPTION OF THE SEVERAL VIEWS OF THE DRAWING

FIG. 2 shows the wound retractor of FIG. 1 in a side view in the clamping position of all the quick-action clamping clips, in a side view, FIG. 3 shows the wound retractor according to FIG. 2 in a setting position and a removal position of the two quick-action clamping clips of the holding arms.

DESCRIPTION OF THE INVENTION

Figure 1:
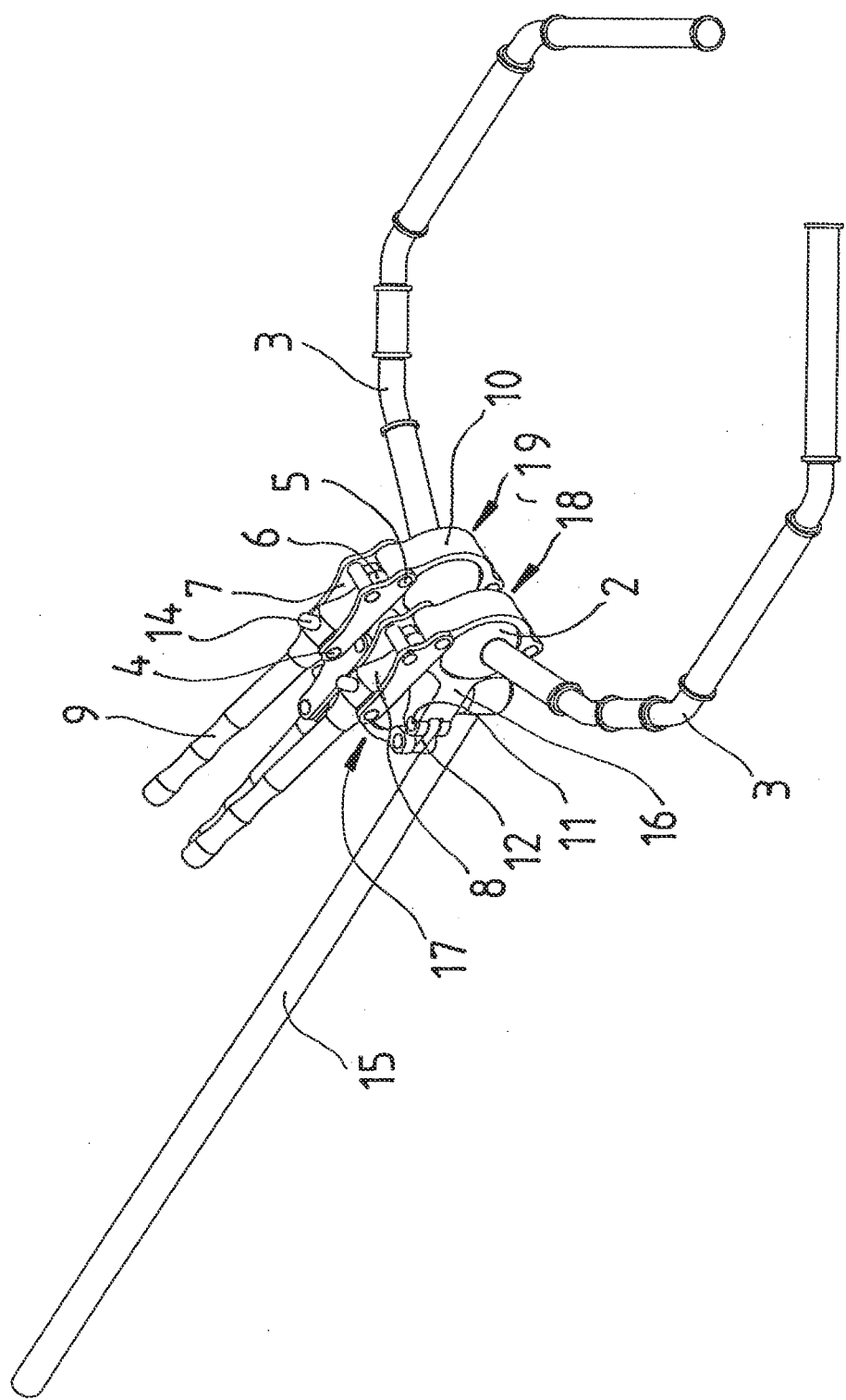
FIG. 1 shows a wound retractor having three quick-action clamping clips in a three-dimensional view.
Figure 4:
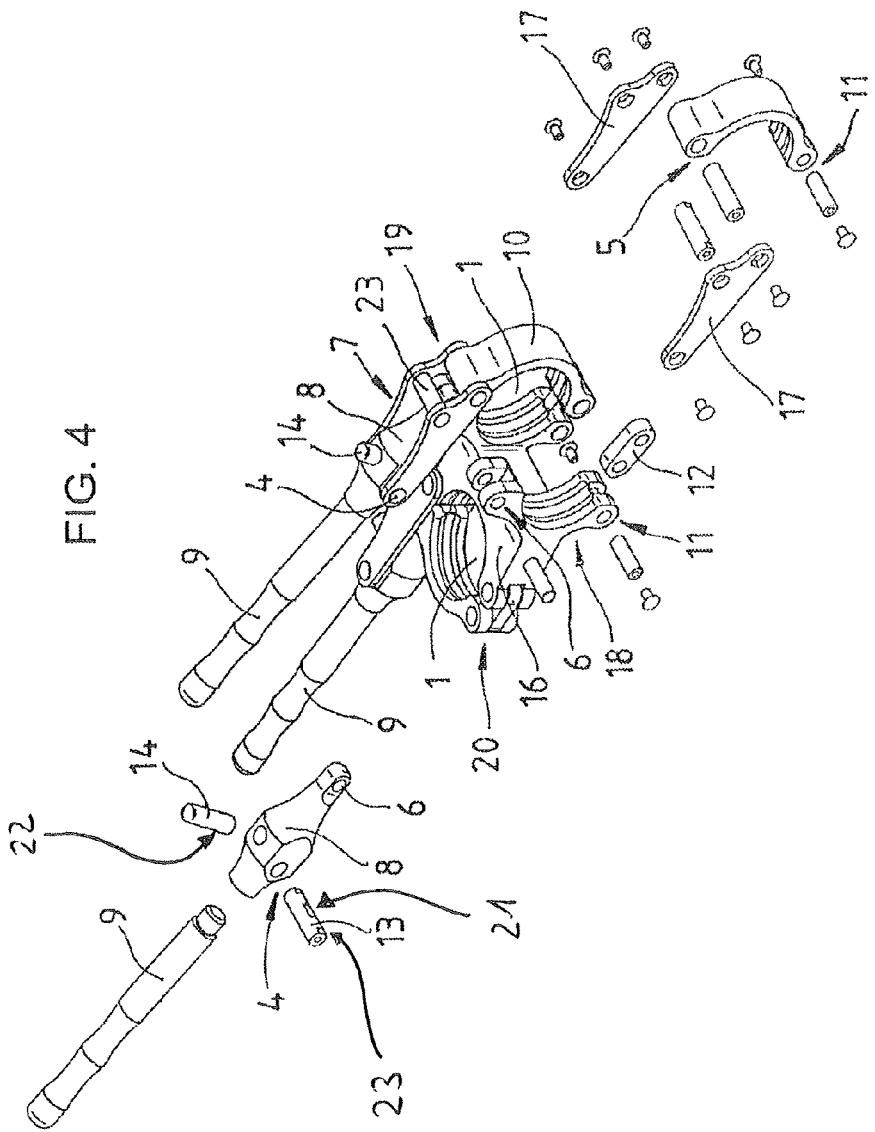
FIG. 4 shows an exploded drawing of a quick-action clamping clip of a central clip consisting of three quick-action clamping clips, in a 3D view.

The wound retractor shown consists of a central clip 16 having three quick-action clamping clips 18; 19; 20, each of which clamps a ball joint 2, of which ball joints 2 the one assigned to the rear quick-action clamping clip 20 belongs to a connecting arm 15 for fastening the wound retractor to a central holder on an operating table and the other two joint balls 2 belong to holding arms 3 which define a wound retraction frame.

Every single one of the three quick-action clamping clips 18; 19; 29 present is designed like a pipe clamp 10, each of which is designed as a receptacle 1 for a joint ball 2 and encloses the latter virtually completely, wherein attachment joints 5; 6 are arranged on the ends of the pipe clamp 10 located opposite one another at only a slight distance apart, in which attachment joints the articulated levers 7; 8 both extend together to the rear in an approximately tangential direction and are connected to one another there via the connecting joint 4. In this case, the articulated lever 7 consists of two separate straps 17 which are fixed on both sides on the outside to the first attachment joint 5 and to the second articulated lever 8, which is designed as a bar and which extends rectilinearly further to the rear and forms the actuating lever 9.

The two straps 17 producing the articulated lever 7 are connected to a further holding pivot 23, which at the same time serves as a motion limit for the actuating lever 9 in the closing direction, specifically for slightly beyond a clamping position, such that a type of self-locking of the toggle fastener is produced in the clamping position of the actuating lever 9.

The pivot of the connecting joint 4 is mounted in the straps 17 in a rotationally fixed manner and is designed as a locking shaft 13 in such a way that pivoting of the actuating lever 9 and thus of the articulated lever 8 about the connecting joint 4 can be locked by a locking pin 14 which has latching surfaces corresponding with the locking shaft 13. The actuating lever 9 is clamped in a setting position of a holding arm, such that the toggle fastener can be opened only to a limited extent without actuating the locking pin 14, i.e. the holding arms move and are set against a slight frictional force, but cannot be removed from the receptacle 1. After the locking pin 14 is actuated, the toggle fastener can be completely opened and the joint ball 2 can be removed from the receptacle 1.

For easier exchange of the joint ball 2, the pipe clamp is provided, in a region opposite the attachment joints 5; 6, with two further joints 11 and a coupling element 12 arranged in between, as a result of which there are, in particular at the central clip 16 shown in the figures, a virtually fixed clip part and three clamping stirrups, linked thereto, as movable parts.

Not shown in the drawings are further quick-action clamping clips in which clamping methods functioning via threads or eccentrics are replaced by toggle fasteners, which can be effected in all known quick-action clamping clips.

The invention claimed is:

1. A quick-action clamping clip of a wound retractor for producing a clamping force, the clamping clip comprising:
   at least one clampable receptacle for at least one of a holding arm or a joint ball of a holding arm;
   a connecting joint;
   first and second attachment joints;
   components;
   a toggle fastener having first and second articulated levers being connected to one another by said connecting joint and having free ends being linked by said attachment joints to said components to permit said components to be moved away from and toward one another;
   one of said articulated levers having an actuating lever configured to be operated manually;
   said first articulated lever having two spaced-apart straps disposed on both sides of said first attachment joint and said connecting joint;
   a locking shaft disposed in said connecting joint, said locking shaft having a releasable latching device configured to mutually lock movement of said first and second articulated levers, said locking shaft being mounted in said straps in a rotationally fixed manner and said locking shaft having a latching surface; and
   a releasable locking pin extended through said connecting joint at a right angle and in an axially offset manner transversely to said locking shaft, said locking pin having a corresponding latching surface engaging said latching surface of said locking shaft and locking the quick-action clamping clip with a slight clamping force in a non-actuated state of said locking pin and permitting the quick-action clamping clip to be opened in an actuated state of said locking pin.

2. The quick-action clamping clip according to claim 1, wherein said actuating lever is aligned with said connecting joint and a first of said attachment joints that is closer to said connecting joint.

3. The quick-action clamping clip according to claim 1, wherein:
   said receptacle is constructed as a pipe clamp partly enclosing said at least one of the holding arm and the joint ball;
   said attachment joints are arranged on the ends of said pipe clamp opposite one another at a slight distance apart;
   both said articulated levers extend to a common side of said clamp and are connected to one another by said connecting joint;
   said attachment joints and said connecting joint have pivots aligned in a clamping position, and said pivots are held pressed toward one another; and,
   said pivot of said connecting joint, in a fixed or removed position of said holding arm, is deflected from its position in a radial direction.

4. The quick-action clamping clip according to claim 3, further including;
   a coupling element;
   said pipe clamp, in a region opposite said attachment joints, having at least a further joint connected by said coupling element and permitting said pipe clamp to be partially opened in said non-actuated state of said locking pin.

5. A central clip for use with a central holder of an operating table, the central clip comprising:
   three quick-action clamping clips constructed according to claim 1;
   two holding arms; and
   a connecting arm for connection to the central holder.

6. The quick-action clamping clip according to claim 1, which further comprises:
   a pipe clamp having a band-shape that substantially encloses the receptacle and has extensions which run substantially tangential and crosswise and carry said attachment joints; and
   said articulated levers are angled and connected to one another by said connecting joint such that compressive forces are produced in the articulated levers when said connecting and attachment joints are aligned, the compressive forces causing tensile forces in ends of the extensions that constrict the pipe clamp.

7. The quick-action clamping clip according to claim 1, wherein:
   said clip is constructed with spreadable forceps; and
   said attachment joints have actuating handles, arranged such that, upon alignment of said attachment joints and said connecting joint, a clamping force is produced on a head of the forceps, which is the shape of the receptacle.

8. The quick-action clamping clip according to claim 1, which further comprises:
   mutually parallel beams having ends;
   the clip has a U-shaped body;
   the receptacle is arranged in the ends of the beams; and
   a clamping pin extends behind transversely through the beams, said clamping pin is supported on an outer side on one of the beams and has on the opposite outer side a further attachment joint for a first of said articulated levers, a second of said articulated levers is arranged on the beam facing the further attachment joint at a second of said attachment joints, and both said articulated levers are connected to one another in an angled manner by the connecting joint, and the joints are arranged such that, when they are aligned, they produce a clamping force which compresses the receptacle.

9. The quick-action clamping clip according to claim 1, wherein:
   said actuating lever is clamped in a setting position of said holding arm, permitting said toggle fastener to be opened only to a limited extent without actuating said locking pin and permitting said holding arm to move and be set against a slight frictional force, but preventing said holding arm from being removed from said receptacle; and
   said toggle fastener is configured to be completely opened to permit said joint ball to be removed from said receptacle after actuating said locking pin.

10. The quick-action clamping clip according to claim 1, wherein:
    said receptacle is constructed as a pipe clamp partly enclosing said at least one of the holding arm and the joint ball; and
    said pipe clamp, in a region opposite said attachment joints, has further joints connected by a coupling element and permitting said pipe clamp to be partially opened in said non-actuated state of said locking pin.

* * * * *